United States Patent [19]
Adler et al.

[11] 4,016,249
[45] Apr. 5, 1977

[54] BONE SEEKING TECHNETIUM 99M COMPLEX

[75] Inventors: Norman Adler, Arlington; Leopoldo Lazaro Camin, Lexington, both of Mass.

[73] Assignee: New England Nuclear Corporation, Boston, Mass.

[22] Filed: Oct. 26, 1973

[21] Appl. No.: 410,086

Related U.S. Application Data

[62] Division of Ser. No. 288,577, Sept. 13, 1972, Pat. No. 3,851,044.

[52] U.S. Cl. .............................. 424/1; 252/301.1 R; 423/249; 424/1.5; 250/303
[51] Int. Cl.² ................. A61K 29/00; A61K 43/00; G01T 1/161
[58] Field of Search .................. 424/1; 423/2, 249; 252/301.1 R; 250/303

[56] References Cited
OTHER PUBLICATIONS

Subramanian et al., Radiology, vol. 99, No. 1, Apr. 1971, pp. 192–196.

*Primary Examiner*—Benjamin R. Padgett
*Assistant Examiner*—Christine M. Nucker

[57] ABSTRACT

A technetium-99m-stannous-phosphate complex in which the phosphate moiety includes pyrophosphate and in which no more than 5 to 15% or 20% by weight of such phosphate moiety is a linear polyphosphate of molecular weight greater than pyrophosphate, a method of making the same, a method of using the same by in vivo intravenous administration to a mammal of the sterile, nonpyrogenic complex followed by radioassay scanning or imaging the skeletal structure, and a kit made up of a stannous-phosphate complex in which the phosphate moiety is pyrophosphate and in which no more than 5 to 15% or 20% by weight of such phosphate moiety is a linear polyphosphate of molecular weight greater than pyrophosphate.

37 Claims, No Drawings

BONE SEEKING TECHNETIUM 99M COMPLEX

This is a division of application Ser. No. 288,577, filed on Sept. 13, 1972, now U.S. Pat. No. 3,851,044.

BACKGROUND OF THE INVENTION

It has been known for some time that phosphates, including long chain linear polyphosphates, when introduced into the blood stream of mammals will selectively seek out and collect in the bone or skeletal structure. Pro. Soc. Exp. Biol Med. Volume 100, pages 53–55 (1959); Journal of Labelled Compounds, April–June 1970, Vol. VI, No. 2, pages 166–173; Journal of Nuclear Medicine, Vol. 11, No. 6, pages 380–381, 1970; Journal of Nuclear Medicine, Vol. 1, No. 1, January 1960, pages 1–13. In these cases a phosphorous atom or atoms of the phosphate are radioactive, i.e. $^{32}P$.

It has also been known for some time that technetium-99m ($^{99m}Tc$) is a preferred radionuclide for radioactively scanning organs because of its short half life and because it radiates gamma rays which can be easily measured, compared, for example, to beta rays. See Radiology, Vol. 99, April 1971, pages 192–196.

It has also been known for some time to use divalent stannous tin ($Sn^{++}$) in the form of stannous chloride, or divalent iron ($Fe^{++}$) or reduced zirconium to bind radioactive $^{99m}Tc$ to carriers, such as chelating agents, red blood cells, albumin and other proteins, which selectively seek out certain organs of the body, in order to carry the $^{99m}Tc$ with them to such organs of the body where it is concentrated, whereby such organ can be radioactively scanned or imaged for diagnostic or other purposes, e.g. radioactive treatment of a pathological condition. See Journal of Nuclear Medicine, Vol. 11, No. 12, 1970, page 761; Journal of Nuclear Medicine, Vol. 12, No. 1, 1971, pages 22–24; Journal of Nuclear Medicine, Vol. 13, No. 2, 1972, pages 180–181; Journal of Nuclear Medicine, Vol. 12, No. 5, May 1971, pages 204–211; Radiology, Vol. 102, January 1972, pages 185–196; Journal of Nuclear Medicine, Vol. 13, No. 1, 1972, pages 58–65.

Also, it has been suggested to label a stannous compound with $^{99m}Tc$ for radioactively imaging bone marrow, Journal of Nuclear Medicine, Vol. 11, 1970, pages 365–366.

It has also been known for some time that the stannous ion $Sn^{++}$ forms soluble complexes with long chain polyphosphates, Journal Inorganic Nuc. Chem., Vol. 28, 1966, pages 493–502.

It has been suggested to employ the aforesaid $^{99m}Tc$ for radioactively scanning the skeletal bone structure of mammals by complexing or binding it to tripolyphosphate carrier by use of the aforesaid stannous ion as a binding agent in order for such phosphate to selectively carry the $^{99m}Tc$ to, and concentrate it in, the skeletal bone structure upon in vivo intravenous administration for subsequent radioactive scanning or imaging the skeletal structure. Radiology, Vol. 99, April 1971, pages 192–196. The use of $^{99m}Tc$ in this manner is alleged to have certain advantages over the use of strontium, e.g. $^{85}Sr$, as the radioactive label which has been used for radioactive bone scanning in the past. These advantages are those which are inherent in $^{99m}Tc$, i.e. short half life and pure, near optimal energy gamma rays. However, the bone uptake (the percent of the total dosage which becomes concentrated in the skeletal structure within a certain time after in vivo intravenous administration) of such $^{99m}Tc$-containing complex and the ratios of such bone uptake of the $^{99m}Tc$ by the other organs of the body (the higher these ratios the better), i.e. radioactive contrast, are not nearly as high as with radioactive strontium.

STATEMENT OF THE INVENTION

It has been discovered that if the phosphate moiety of the $^{99m}Tc$-stannous-phosphate complex, which has been suggested in the aforesaid Radiology publication, comprises pyrophosphate ($P_2O_7^{-4}$) (which is a linear polyphosphate moiety of molecular weight less than 300), the bone uptake, bone/blood ratio, bone/liver ratio, bone/G.I. ratio and bone/kidneys ratio are substantially increased.

It has also been discovered that optimum results are achieved if such phosphate moiety contains no more than about 15 to 20 or 25%, preferably no more than 5 to 10% and more preferably no more than 5% (less than 5% is the most preferred), by weight of linear or branched chain polyphosphate (formula $P_nO_{3n+1}^{-(n+2)}$) of molecular weight greater than that of pyrophosphate.

Maximum bone/liver ratios are achieved when the $^{99m}Tc$-$Sn^{++}$-pyrophosphate complex is administered to the mammal in relatively small dosages of substantially less than 20 or 25, preferably substantially less than 8 or 10 and still more preferably less than 5 or 6 (between 0.01 or 0.10 and 3 and even less provide excellent results), milligrams pyrophosphate moiety per kilogram of body weight of the mammal.

The term "phosphate moiety" as used herein refers to the phosphorus and oxygen atoms only of the phosphate.

The presence of polyphosphates of formula $P_nO_{3n+1}^{-(n+2)}$ and molecular weight greater than that of pyrophosphate seems to reduce bone take-up and the aforesaid ratios, as compared to complexes without such higher molecular weight polyphosphates. However, as aforesaid, some of such higher molecular weight polyphosphates can be tolerated, preferably not more than about 15% to 20% or 25%, more preferably no more than 5% to 10% and still more preferably not more than 5% (less than 5% is the most preferred), by weight of the total phosphate moiety.

Where the pyrophosphate does not constitute 100% of the phosphate moiety of the $^{99m}Tc$-$Sn^{++}$-phosphate complex, the rest of the phosphate moiety is preferably a ring phosphate of formula $p_nO_{3n}^{-n}$ (with $n$ preferably being 3 which is trimetaphosphate) and/or ortho phosphate, and preferably a ring phosphate only, although the aforesaid limited amounts of higher molecular weight linear polyphosphates can be tolerated.

The complex is made from a water soluble alkali metal (preferably sodium) or ammonium salt or acid salt of the pyrophosphate, e.g. sodium pyrophosphate.

Preferably, the sodium pyrophosphate is admixed with a stannous salt, e.g. $SnCl_2$ (the stannous salts of other acids which are pharmaceutically acceptable, i.e. safely intravenously administered, can be used) to form the stannous-pyrophosphate complex, the pH of which is adjusted to 3–8, preferably 5–8, by a pharmaceutically acceptable acid, such as HCl, or base, such as NaOH or $Na_2CO_3$ or $NaHCO_3$, followed by admixing with the stannous-pyrophosphate complex, an aqueous saline solution of radioactive sodium pertechnetate ($^{99m}Tc$) to form the $^{99m}Tc$-stannous-pyrophosphate complex at the time it is desired to intravenously administer the $^{99m}$Tc complex. The stannous-pyrophosphate complex may be sealed in a sterile, non-pyrogenic container or vial as a solution or a lyophilized solid and shipped as a kit with the freshly generated sterile and non-pyrogenic $^{99m}$Tc being added aseptically at the situs just prior to use.

DETAILED DESCRIPTION OF INVENTION (INCLUDING EXAMPLES)

The following compositions were prepared:

TABLE I

| Sample No. | Description |
|---|---|
| 1 | A commercial sodium polyphosphate sold by FMC Corporation under the trade name FMC Glass H (average chain length of 21 and average M.W. about 2100). |
| 1–1 | A first high molecular weight fraction of the FMC Glass H of Sample 1 obtained by fractionating an aqueous solution of Sample 1 with acetone according to the technique described in Van Wazer, Phophorous And Its Compounds, Interscience Publishers, Inc. 1961 (pages 744–747) to precipitate out of the aqueous solution of the FMC Glass H, as an oil, the highest molecular weight fraction of polyphosphates (composition given in TABLE 2). |
| 1–2 | A second acetone fraction of FMC Glass H achieved by adding more acetone to precipitate out of the remaining supernatant of 1–1, as an oil, the next higher molecular weight polyphosphates (composition given in TABLE 2). The acetone decreases the solubility of the polyphosphates in the water; the higher the molecular weight of the polyphosphate the less soluble it is so that the highest molecular weights are forced out of solution first. |
| 1–3 | A third acetone fraction of FMC Glass H containing the next higher molecular weight polyphosphates is precipitated out of the remaining supernatant solution of 1–2, as an oil, upon addition of further amounts of acetone (composition given in TABLE 2). |
| 1–4 | A fourth acetone fraction of FMC Glass H containing the next higher molecular weight polyphosphates (composition given in TABLE 2) is precipitated out of the supernatant solution of 1–3, as an oil, by adding more acetone. |
| 1–5 | A fifth acetone fraction of the FMC Glass H (containing the next higher molecular weight polyphosphates) (composition given in TABLE 2) is precipitated out of the remaining supernatant solution of 1–4, as an oil, by adding more acetone. |
| 1–6 | A sixth acetone fraction of FMC Glass H (composition given in TABLE 2) is precipitated out of the remaining supernatant solution of 1–5, as a solid precipitate of the next higher molecular weight polyphosphates by adding more acetone. |
| 1–7 | A seventh acetone fraction of FMC Glass H (composition given in TABLE 2) is precipitated out of the remaining supernatant solution of 1–6, as a solid precipitate of the next higher molecular weight polyphosphates by adding more acetone. |
| 1–8 | The residue fraction in the supernatant liquid left after removal of the 1–7 fraction (composition given in TABLE 2) is recovered by evaporating off the supernatant liquid. |
| 2 | An end acetone fraction of Sample 1 after 90% by weight had been previously fractionated off and leaving after removal of such end fraction 3% by weight in the supernatant (composition given in TABLE 2). |
| 4 | A mixture of 86% sodium trimetaphosphate ($Na_3P_3O_9$), 3% sodium orthophosphate ($Na_3PO_4$) (molecular weight of phosphate moiety - 95) an 10% sodium pyrophosphate ($Na_4P_2O_7$) (liner polyphosphate - molecular weight of phosphate moiety - 174) obtained by acetone fractionation of sodium trimetaphosphate obtained from Monsanto. Sodium trimetaphosphate, as aforesaid, is one of a plurality of cyclic phosphates having the general formula $P_nO_{3n}^{-n}$. Sodium orthophosphate is a phosphate monomer. Sodium pyrophosphate is a dipolyphosphate. |
| 5 | An acetone end fraction of a food grade polyphosphate sold by FMC under the name FMC FG (composition given in TABLE 2). |
| 6 | A commercial cyclic trimetaphosphate sold by Stauffer Chemical. (composition given in TABLE 2). |
| 7 | Sodium orthophosphate. |
| 8 | Sodium pyrophosphate. |
| 9 | Sodium tripolyphosphate |
| 10 | Sodium tetrapolyphosphate - $Na_6P_4O_{13}$ - a polyphosphate - phosphate moiety having a M. W. of 348. It, together with the pyrophosphate and tripolyphosphate, fall in the class of linear chain polyphosphates having the general formula $P_nO_{3n+1}^{-(n+2)}$. |

An aqueous solution of each of the phosphate composition samples 1 through 10 (40 mg. phosphate/1 ml.

solution) were made with distilled water in which the dissolved oxygen content was reduced in a conventional manner by bubbling through such water gaseous nitrogen for a period of two hours. The water and phosphates were mixed to form the solutions in a nitrogen atmosphere and in a nitrogen flushed container. The reason for this is to reduce oxidation of the divalent $Sn^{++}$ to be subsequently admixed with each solution sample. However, it is not essential (but high preferred) to use nitrogen-treated water or a nitrogen atmosphere or a nitrogen-flushed container. Other known pharmaceutically acceptable conditions, which will inhibit oxidation of the $Sn^{++}$ upon subsequent mixing thereof with the phosphate solution, can be used, including the use of conventional pharmaceutically acceptable reducing agents and anti-oxidants in the products used.

Each of these solutions, samples 1 through 10, in an amount equal to 100 ml, was mixed with 0.16g of solid $SnCl_2.2H_2O$ under a nitrogen atmosphere. The $SnCl_2.2H_2O$ was made by adding to 84.5 mg. of metallic tin, sufficient concentrated HCl with mixing until all the tin has dissolved followed by removing excess acid and water by lyophilization (this operation also being carried out in a vacuum or in a nitrogen atmosphere and in a nitrogen flushed container to prevent oxidation of stannous to stannic). Antioxidants, which can be administered intravenously, may also be used. A stannous ($Sn^{++}$)-phosphate complex or mixture of some kind was formed in each case, the phosphate moiety of each sample corresponding to the phosphate moieties of the phosphates set forth in TABLE 2.

Sufficient aqueous solution 3N sodium hydroxide (sodium carbonate or bicarbonate can also be used), in the case of samples 1 through 7 and 9 and 10, and 3N HCl, in the case of sample 8, is then added to each sample to give a pH of 5.0 to achieve a pH suitable for subsequent intravenous in vivo administration into the body of a mammal, in this case adult mice. The pH adjustment is preferably done under a nitrogen atmosphere also.

After thorough mixing, the solutions are sterilized by passing them through a Millipore biological filter of 0.22 micron pore size under a nitrogen atmosphere. Thereafter milliliter portions of each of the sterile solutions are poured into individual sterile and non-pyrogenic storage glass vials under a nitrogen atmosphere.

In the case of each sample, vials are lyophilized by conventional freeze drying equipment under aseptic conditions to remove water. This provides a solid stannous-phosphate complex which aids in shipping and storage and which is more stable than the complex in solution.

Each vial contains 1.35 mg. $SnCl_2$ and 40 mg. of the phosphate.

The vials can be sealed and stored until needed subsequently to form the technetium-99m-stannous-phosphate complex at the use situs.

To prepare the technetium-99m complex, 3 to 7 (5) ml. of fresh sodium pertechnetate, removed as a sterile non-pyrogenic eluate from a sterile NEN $^{99m}Tc$ Generator (any other source of pharmaceutically acceptable $^{99m}Tc$ can be used, including 99mTc generators manufactured by others than NEN), in a 0.9% saline solution is aseptically added to each vial containing the sterile and non-pyrogenic stannous-phosphate complex and the vial is swirled until a solution is obtained. In each case a technetium-99m-stannous-phosphate complex or mixture of some kind is formed in aqueous solution (8 mg. phosphate per ml solution when 5 ml of pertechnetate is used), the phosphate moiety of which corresponds to the phosphate moieties of the phosphate compounds of each sample set forth in TABLE 2.

Aseptic techniques and sterile, non-pyrogenic ingredients and containers were used at all steps, such procedures being standard to those skilled in the art.

An eleventh sample was prepared in the manner set forth above by diluting sample 8 to a concentration of 1 mg of phosphate per ml of solution. This was labeled Sample 11.

Each of the technetium-99m-stannous-phosphate complex-containing solutions is aseptically intravenously injected in vivo into a vein in the tail of adult mice (average weight 0.040 kgs) in an amount equal to between 1 and 3 mCi and a volume of 0.12 ml (8 mg. of phosphate per ml solution in samples 1 through 10 and 1 mg. phosphate per ml. solution in sample 11). Also sample 8 was injected in the same manner except that a volume of 0.015 ml was injected instead of 0.12 ml to reduce the dosage of the complex by a factor of 8. This was labeled Sample 12.

Three hours after intravenous administration, some of the mice to which each sample was administered were sacrificed and the various organs of their bodies (skeletal, liver, G.I., blood, kidneys) were counted by conventional gamma ray counting techiques to determine uptake of $^{99m}Tc$ by each organ and thereby determine contrast of bone uptake as compared to uptake by the other organs. As aforesaid, it is not only important to have a high bone uptake (based on total technetium-99m-dosage but it is also important that the ratio of uptake by the bone to uptake by the other organs be high.

The results are set forth in TABLE 2 below, in which the uptakes (the bone uptake figures represent the average bone uptake for the skeletal system) are in terms of percent of the total technetium-99m activity injected (corrected for radioactive decay) which has collected in the various organs indicated three hours after in vivo intravenous injection, in which the ratio amounts are computed from the uptake amounts adjusted to compensate for the different weights of the organs and the different weights of the animals by dividing each uptake amount by the ratio expressed in percentage of the weight of such organ to the weight of the animal, in which "Percent Having Phosphate Moiety M. W. Less Than 300" refers to weight percent of the phosphate moiety based on the total phosphate moiety of the sample identified in the first horizontal column, in which the percents referred to under Phosphate Composition are weight percents of the whole phosphate moiety of the sample (as aforesaid, phosphate moiety as used herein is limited to that part of the compound or complex made up of phosphate phosphorus and oxygen atoms), in which Ortho P1 refers to the phosphate moiety of sodium orthophosphate, Pyro P2 refers to the phosphate moiety of sodium pyrophosphate, Tripoly P3 refers to the phosphate moiety of sodium tripolyphosphate, Tetrapoly P4 refers to the phosphate moiety of sodium tetrapolyphosphate, Trimeta R3 refers to the phosphate moiety of sodium trimetaphosphate, Tetrameta R4 refers to the phosphate moiety of sodium tetrametaphosphate, both trimeta and tetrametaphosphates falling within the class of cyclic or ring phosphates having the formula $P_3O_{3n}^{-n}$, in which "Pentapoly And Longer Linear Chains" refers to the phosphate moiety of sodium pentapolyphosphate and longer linear (linear as used herein includes straight and branched linear phosphate chains) polyphosphates of formula $P_nO_{3n+1}^{-(n+2)}$, in which "Average M.W." refers to the average molecular weight of the phosphate moiety of the sample and in which "Fraction In Raw Stock" with reference to samples 1-1, 1-2, 1-3, 1-4, 1-6, 1-7 and 1-8 refer to the normalized percent by weight of each of these samples in sample 1, which is the raw stock which is fractionated.

Localized areas of abnormal accumulation of the radio-pharmaceutical may be seen in primary malignancies of the bone, metastatic malignanacies of the bone, acute or chronic osteomyelitis, arthritides, recent fractures, areas of ectopic calcification, Paget's disease, regional migratory osteoporosis, areas of aseptic necrosis and in general any pathological situation involving bone in which there is increased osteogenic activity or localized increased osseous blood perfusion.

The acute toxicity level in mice ($LD_{50/30}$) for Sample No. 2 has been determined to be 150 mg/Kg body

TABLE 2

| Phosphate Sample | 1 FMC | 1-1 | 1-2 | 1-3 | 1-4 | 1-6 | 1-7 | 1-8 | 2 | 4 | 5 | 6 | 7 | 8 | 9 | 10 | 11 | 12 |
|---|---|---|---|---|---|---|---|---|---|---|---|---|---|---|---|---|---|---|
| Uptake | | | | | | | | | | | | | | | | | | |
| Blood | 1.7 | 4.0 | 4.2 | 4.6 | 2.9 | 3.4 | 1.3 | 1.3 | 1.6 | 1.3 | 0.65 | 1.0 | 4.5 | 1.2 | 1.8 | 3.3 | 1.4 | 1.1 |
| Liver | 23 | 2.7 | 2.7 | 2.8 | 2.2 | 6.8 | 0.9 | 2.0 | 1.3 | 1.3 | 0.52 | 0.85 | 5.9 | 7.5 | 1.3 | 4.7 | 1.2 | 0.8 |
| G.I. | 4.9 | 8.5 | 5.5 | 7.5 | 4.2 | 4.8 | 1.8 | 1.5 | 2.2 | 1.9 | 0.75 | 1.9 | 1.8 | 1.7 | 2.2 | 4.0 | 1.8 | 2.5 |
| Kidneys | 3.6 | 3.7 | 3.1 | 3.2 | 1.7 | 2.6 | 0.9 | 0.9 | 1.1 | 1.5 | 0.88 | 0.82 | 1.1 | 1.3 | 1.5 | 3.1 | 1.3 | 3.0 |
| Av. Bones | 17 | 35 | 31 | 32 | 31 | 35 | 45 | 65 | 53 | 70 | 70 | 57 | 20 | 56 | 45 | 29 | 82 | 65 |
| Ratios | | | | | | | | | | | | | | | | | | |
| Bone/Blood | 5 | 4 | 4 | 4 | 5 | 5 | 18 | 29 | 17 | 30 | 58 | 32 | 2 | 34 | 13 | 5 | 35 | 24 |
| /Liver | 0.5 | 7 | 6 | 7 | 8 | 3 | 29 | 19 | 24 | 32 | 78 | 38 | 2 | 5 | 20 | 3 | 47 | 36 |
| /G.I. | 5 | 6 | 8 | 7 | 11 | 11 | 37 | 63 | 36 | 55 | 140 | 55 | 17 | 49 | 31 | 11 | 81 | 32 |
| /Kidneys | 1 | 1 | 1 | 1 | 3 | 2 | 9 | 12 | 8 | 9 | 13 | 12 | 3 | 9 | 5 | 1 | 12 | 6 |
| Percent Having Phosphate Moiety M.W. Less Than 300 | 15% | 3% | 3% | 5% | 13% | 17% | 90% | 100% | 55% | 99 | 98 | 98 | 100 | 100 | 100 | 10 | 100 | 100 |
| Phosphate Composition | | | | | | | | | | | | | | | | | | |
| Ortho $P^1$ (%) | 3 | 1.0 | 1 | 2 | 5 | 5 | 10 | 50 | 5 | 3 | 15 | 4.0 | 100 | 0 | 0 | 0 | 0 | 0 |
| Pyro $P^2$ (%) | 2 | 0.5 | 0.5 | 1 | 2 | 1 | 15 | 10 | 10 | 10 | 5.0 | 8.0 | 0 | 100 | 0 | 0 | 100 | 100 |
| Tripoly $P^3$ (%) | 2 | 0.5 | 0.5 | 1 | 2 | 1 | 5 | | | 0 | 0 | 0 | 0 | 0 | 100 | 0 | 0 | 0 |
| Tetra Poly $P^4$ (%) | 2 | 0.5 | 0.5 | 1 | 3 | 10 | 5 | | | 1 | 0 | 1.0 | 0 | 0 | 0 | 90 | 0 | 0 |
| Trimeta $R^3$ (%) Cyclic | 8 | 0.5 | 0.5 | 1 | 4 | 10 | 60 | 40 | 40 | 86 | 78 | 86 | 0 | 0 | 0 | 0 | 0 | 0 |
| Cyclic Tetra Meta $R^4$ (%) | 4 | 0.5 | 0.5 | 1 | 4 | 50 | 5 | | 40 | | 0 | 0 | 0 | 0 | 0 | 10 | 0 | 0 |
| Penta Poly $P^5$ & Longer Linear Chains | 79 | 96.5 | 96.5 | 93 | 80 | 23 | 0 | 0 | 5 | | 2 | 1 | 0 | 0 | 0 | 0 | 0 | 0 |
| Average M.W. | 2100 | 3900 | 2700 | 1800 | 1200 | | | | | | | | | | | | | |
| Fraction in Raw Stock | 100 | 3.5 | 61 | 16.2 | 7.5 | 5.0 | 6.1 | 0.7 | | | | | | | | | | |

Conventional gamma counting techniques for measuring technetium 99m take-up in the organs are conventional gamma ray-excitable scintillation counters for radioassaying multiple samples of the organs of the sacrificed mice.

Also, conventional scanning by radioactive imaging using a gamma ray-excited scintillation or gamma camera and a dual crystal rectilinear scanner was used in vivo. In vivo scintiphotos of the total body using the Anger camera were obtained as well as rectilinear total body scans.

The figures given in TABLE 2 are average figures achieved by the aforesaid conventional counting techniques, each sample having been intravenously administered to mice followed by radioactive counting.

Following intravenous administration, the $^{99m}$Tc-Sn$^{++}$-pyrophosphate complexes of the present invention are rapidly cleared from the blood by deposition in bone and excretion into urine. Thus, the technetium-99m-stannous-pyrophosphate complexes are metabolizable. The deposition of the $^{99m}$Tc-stannous-pyrophosphate complexes of the invention appears to be primarily a function of the bone blood flow as well as being related to the efficiency of the bone in extracting the complex from the blood which perfuses the bones.

It was observed that the deposition of the $^{99m}$Tc in the skeleton is bilaterally symmetrical with increased accumulations being present in the axial skeleton as compared to the appendicular skeleton. There is also increased deposition in the distal aspect of long bones.

weight and for Sample 6 it is 800 mg/Kg and for Sample 8 it is 70 mg/Kg. Subacute toxicity studies in mice of Sample 2 have shown no signs of toxicity after 15 daily injections at dose levels as high as 63 mg/Kg body weight/day. A similar subacute study in dogs indicates no signs of toxicity at a dose level of 3.6 mg/Kg body weight/day.

It was found that samples 4 and 6 were only one fourth as toxic to mice as sample 2 and one-eighth as toxic to mice as sample 1.

The complexes of the invention have been used successfully as a skeletal imaging or scanning agent to visualize areas of altered blood flow to the bone and altered osteogenic activity, including suspected bone lesions not shown on X-ray, bone survey performed as part of a work-up in patients with known or suspected malignancy, to follow the response of metastatic or primary bone lesions to radiation therapy, metabolic bone disease, to diagnose arthritis and osteomyelitis, and to diagnose and determine healing rate of bone fractures.

The technetium-99m ($^{99m}$Tc) labeling reactions involved in preparing the $^{99m}$Tc-stannous-phosphate complexes of the invention depend on maintaining the tin in the reduced or stannous (Sn$^{+2}$) state. Oxidants present in the pertechnetate supply may adversely affect quality.

The radioactive dosage of the $^{99m}$Tc complex of the invention may vary from 1 to 25 mCi (millicuries) but preferably is from 10 to 15 mCi. The dosage should preferably be substantially less than 20 or 25, preferably less than 8 or 10 and more preferably less than 5 or 6 mg. of pyrophosphate moiety per kilogram of body weight of the mammal since greater pyrophosphate dosages than this reduces the bone-liver ratio too much. Note for example the low bone-liver ratio in sample 8 where the dosage was 25 mg. pyrophosphate per Kg body weight compared to the bone-liver ratio of sample 11 where the dosage was 3.1 mg/Kg body weight.

Only trace amounts of pyrophosphate moiety in the dosage, e.g. as low as 0.001, more preferably 0.01, mg/Kg body weight, gives good bone take-up and bone-to-other organ take-up ratios.

The dosage of pyrophosphate can be kept small either by use of more dilute dosage solutions of the pure pyrophosphate, as in sample 11 or by administering smaller doses of a more concentrated complex solution, the phosphate moiety of which contains a high concentration of pyrophosphate or by more concentrated solutions of phosphate containing, in addition to the pyrophosphate, ring phosphate and/or orthophosphate which effectively dilute the pyrophosphate concentration of the dose.

It is preferred to use a $^{99m}$Tc-Sn$^{++}$-phosphate solution containing between 0.1 and 40, more preferably between 0.5 and 4 or 5 mgs of pyrophosphate moiety per ml of solution.

An advantage of a complex containing a relatively large amount of ring phosphate and a smaller amount of pyrophosphate is that the ring phosphate in addition to providing excellent bone up-take and bone-to-other-organ ratios is less toxic than pyrophosphate, although pyrophosphate, alone, is still not unduly toxic.

Scanning may be commenced as early as one hour after intravenous administration and may be as long after injection as clinically useful amounts of $^{99m}$Tc remain in the organ.

Another manner of making the complex of the invention is to weigh 4 mg. of SnCl$_2$.2H$_2$O and 100 mg. of sodium pyrophosphate into a flask (the flask is sterile and non-pyrogenic and is flushed with nitrogen before weighing and is kept under nitrogen during this step and for the next step). Add, under aseptic conditions, 12 ml of sterile, non-pyrogenic sodium pertechnetate in 0.9% saline solution. Shake the mixture until a solution is obtained followed by intravenous injection (preferably the pH of the mixture is aseptically adjusted to pH 3–8 before intravenous injection).

Also, the sterile stannous chloride can first be aseptically mixed with the sterile $^{99m}$Tc saline solution to form a $^{99m}$Tc-stannous complex, followed by adding the sterile sodium pyrophosphate under aseptic conditions to form the $^{99m}$Tc-stannous-pyrophosphate, adjusting the pH to 3–8, followed by intravenous injection.

It can be seen from TABLE 2 that a $^{99m}$Tc-stannous-phosphate complex in which the phosphate moiety comprises pyrophosphate and in which such moiety contains no more than 25% by weight of linear polyphosphate of molecular weight greater than that of pyrophosphate (samples 1–7, 1–8, 2, 4, 5 and 6, 8, 11 and 12) gives surprising higher bone uptake and ratio of bone uptake to other organs, as compared to orthophosphate and other polyphosphates, e.g. tripolyphosphate, tetrapolyphosphate and longer chain polyphosphates (see samples 1, 1–2 to 1–6, 7, 9 and 10).

It can also be seen by comprising samples 8, 11 and 12 in TABLE 2 that the bone to liver ratio is substantially increased by reducing the amount of pyrophosphate in the dosage administered to the mammal.

The pyrophosphate moiety of the $^{99m}$Tc-stannous-phosphate complex may be from 1 or 2% or even less up to 100% by weight of the total phosphate moiety. Preferably, the pyrophosphate moiety consists of 5 or 10% or more of the total phosphate moiety, more preferably 50% or 60% or more and most preferably between 90 and 100%.

Although the stannous (Sn$^{++}$) ion is by far preferred, the divalent ferrous (Fe$^{++}$) ion in the form of ferrous ascorbate, and reduced zirconium can also be used but without as good results. All these metals can exist in a plurality of redox states.

The phosphate may be added to the solid SnCl$_2$ as an aqueous solution, or it may be added to a solution of the SnCl$_2$ to form the Sn$^{++}$-phosphate complex followed by adding the $^{99m}$Tc solution.

Very little Sn$^{++}$ need be used to form the complex of the invention, e.g. less than 7 or 10% of the phosphate based on molecular weights.

The weight ratio of Sn$^{++}$ ion to the pyrophosphate moiety may vary over a wide range, i.e. from $10^{-3}$ to 0.50, preferably 0.01 to 0.4. It is preferred that the molecular ratio of Sn$^{++}$ to pryophosphate moiety not exceed 2/1. The maximum ratio is dictated by the amount beyond which the precipitation of Sn$^{++}$ occurs. The minimum amount required is that amount necessary to bind a sufficient amount of $^{99m}$Tc to the pyrophosphate to achieve good bone uptake and contrast. This can be determined by routine experiment.

The pH of the stannous-phosphate complex may be between 3 and 8.

The water used for making the complexes of the invention is distilled and is at an elevated temperature of 200° F during removal of dissolved oxygen and reduction of oxidants by bubbling the nitrogen gas therethrough.

The maximum amount of $^{99m}$Tc is that beyond the capacity of the Sn$^{++}$-pyrophosphate complex to bind the $^{99m}$Tc. This can be determined by routine thin layer radiochromatography to determine the percent of free or unbound $^{99m}$Tc in the complex. The minimum amount is dictated by that amount below which there is an insufficient amount to give good scanning of bone uptake and contrast, which also can be determined by routine experiment. Generally, the amount of $^{99m}$Tc added to the Sn$^{++}$ pyrophosphate complex should be sufficient to achieve the counting rate desired by the doctor or laboratory personnel for the volume to be injected; ordinarily, as aforesaid, the activity dosage varies from 5 to 25 millicuries.

Although sodium pyrophosphates are preferred, any alkali metal, such as potassium and lithium, or ammonium can be used as the cation so long as it is pharmaceutically acceptable so that it can be safely administered intravenously. Also the acid pyrophosphates of such cations can be used.

Although in the examples given above saline water was used as the vehicle, any other vehicle which is pharmaceutically acceptable for intravenous administration can be used.

It is not intended that the invention be limited to any theory which may have been given above or to the specific examples set forth above but only by the claims appended hereto and their equivalents.

We claim:

1. A metabolizable radioactive bone seeking solution for intravenous administration to mammals comprising a technetium-99$^m$-stannous-phosphate complex, the phosphate moiety of which comprises pyrophosphate, said complex being in sterile, non-pyrogenic solution in a pharmaceutically acceptable vehicle at a pH of between 3 and 8, said phosphate moiety containing not substantially more than 25% by weight of linear polyphosphates of formulation $P_nO_{3n+1}{}^{-(n+2)}$ having a molecular weight greater than pyrophosphate.

2. A solution according to claim 1, said phosphate moiety containing not substantially more than 20% by weight of linear phosphates of formulation $P_nO_{3n+1}{}^{-(n+2)}$ having a molecular weight greater than pyrophosphate.

3. A solution according to claim 2, said vehicle also containing a pH adjusting agent acceptable for intravenous injection to maintain said pH of 3 to 8, the concentration of the pyrophosphate moiety in said solution being between 0.1 and 5 mg. per milliliter of solution.

4. A solution according to claim 2, any phosphate in said pyrophosphate moiety other than pyrophosphate being selected from the group consisting of a ring phosphate of formula $P_nO_{3n}{}^{-n}$, orthophosphate and combinations thereof.

5. A method of concentrating $^{99m}$Tc in vivo in the skeletal structure of a mammal comprising intravenously administering to the mammal a metabolizable radioactive bone seeking composition comprising a sterile, non-pyrogenic aqueous solution of technetium-99m-stannous-phosphate complex, the phosphate moiety of which comprises pyrophosphate and contains no more than 25% by weight of linear polyphosphates of formulation $P_nO_{3n+1}{}^{-(n+2)}$ having a molecular weight greater than pyrophosphate.

6. A method according to claim 5, said phosphate moiety being substantially free from said linear polyphosphates.

7. A method according to claim 6, wherein said phosphate moiety comprises substantially 100% pyrophosphate.

8. A method according to claim 5, the concentration of said pyrophosphate in said solution being less than 25 mg per kilogram of weight of said mammal.

9. A method according to claim 8, the concentration of said pyrophosphate in said solution being less than 10 mg per kilogram of weight of said mammal and at least the major portion of any phosphate in said phosphate moiety other than pyrophosphate being selected from the group consisting of a ring phosphate of formula $P_nO_{3n}{}^{-n}$ and orthophosphate and combinations thereof.

10. A method according to claim 9, where $n$ is equal to 3.

11. A method according to claim 5, more than 50% by weight of said phosphate moiety being said pyrophosphate.

12. A method according to claim 8, said phosphate moiety comprising a mixture of said pyrophosphate, a ring phosphate of formula $P_nO_{3n}{}^{-n}$ and an orthophosphate.

13. A method according to claim 12, wherein $n$ is 3.

14. A method according to claim 8, wherein at least about 90% of said phosphate moiety is said pyrophosphate.

15. A method according to claim 8, at least 1% of said phosphate moiety being pyrophosphate and substantially any remaining phosphate moiety comprising phosphate selected from the group consisting of a ring phosphate of formula $P_nO_{3n}{}^{-n}$ and orthophosphate and combinations thereof.

16. A method according to claim 8, at least 5% of said phosphate moiety being said pyrophosphate and substantially any remaining phosphate moiety being selected from the group consisting of a ring phosphate of formula $P_nO_{3n}{}^{-n}$ where $n$ is 3, one or more phosphates of formula $P_nO_{3n+1}{}^{-(n+2)}$ of which not more than 20% by weight has an $n$ value greater than 2 and combinations thereof.

17. A method according to claim 16, wherein said solution has a pH of between 3 and 8.

18. A method according to claim 17, said solution containing a pH adjusting agent acceptable for intravenous injection to maintain said solution at a pH of 3 to 8.

19. A method of obtaining a radioactive $^{99m}$Tc image of the skeletal structure of mammals for diagnostic purposes comprising the steps of intravenously administering in vivo to the mammal a metabolizable radioactive bone-seeking composition comprising a sterile, non-pyrogenic solution of pH between 3 and 8 in a pharmaceutically acceptable vehicle, of a technetium-99m-stannous-phosphate complex, the phosphate moiety of which comprises pyrophosphate, said phosphate moiety containing no more than 25% by weight of linear polyphosphates of formulation $P_nO_{3n+1}{}^{-(n+2)}$ having a molecular weight greater than pyrophosphate, followed by exposing said skeletal structure to a gamma ray sensitive device within a time certain after said intravenous administration to observe the radioactive $^{99m}$Tc image of said skeletal structure for diagnostic purposes.

20. A method according to claim 19, said solution containing less than 25 mgs. of pyrophosphate per kilogram body weight.

21. A method according to claim 20, including the step of aseptically admixing a sterile, non-pyrogenic aqueous solution of sodium pertechnetate containing $^{99m}$Tc with a sterile and nonpyrogenic stannous-phosphate complex having a phosphate moiety as claimed in claim 48 to form said technetium 99m-stannous-phosphate complex shortly before said intravenous administration.

22. A method according to claim 20, in which any phosphate in said phosphate moiety other than pyrophosphate is selected from the group consisting of a ring phosphate of formula $P_nO_{3n}$, and one or more phosphates of formulation $P_nO_{3n+1}{}^{-(n+2)}$, in which $n$ is 2 or less, and combinations thereof.

23. A method according to claim 22, in which at least 5% of the phosphate moiety is pyrophosphate and in which any remaining phosphate is selected from orthophosphate and said ring phosphate and combinations thereof.

24. A method according to claim 21, said pertechnetate solution being a saline solution and being added to said stannous-phosphate complex which is in the form of a freeze dried solid.

25. A method according to claim 20, said phosphate moiety being substantially 100% pyrophosphate.

26. A method of making a metabolizable radioactive bone seeking composition for intravenous administration to mammals comprising admixing a stannous compound with a phosphate, the phosphate moiety of which is pryophosphate to form a stannous-phosphate complex, the phosphate moiety of which is substantially the same as that of said phosphate, said phosphate moiety containing no more than 25% by weight of linear polyphosphates of formulation $P_nO_{3n+1}^{-(n+2)}$ having a molecular weight greater than pyrophosphate, adjusting the pH of the complex to between 3 and 8, sterilizing the complex, adding to the sterile complex a sterile, non-pyrogenic aqueous solution of sodium pertechnetate containing $^{99m}Tc$ to form a $^{99m}Tc$-stannous-phosphate complex for intravenous administration to mammals.

27. A method according to claim 26, said phosphate moiety being substantially free from said linear polyphosphates.

28. A method according to claim 26, the concentration of pyrophosphate in said last mentioned solution being between 0.1 and 5 mg. per liter of solution.

29. A method according to claim 26, at least 5% of said phosphate moiety being pyrophosphate and at least the major portion of any remaining phosphate moiety being selected from the group consisting of orthophosphate and a ring phosphate of formula $P_nO_{3n}^{-n}$ and combinations thereof.

30. A method according to claim 29, where $n$ is equal to 3.

31. A method according to claim 26, substantially 100% by weight of said phosphate moiety being said pyrophosphate.

32. A method according to claim 26, said phosphate moiety comprising a mixture of said pyrophosphate, orthophosphate and a ring phosphate of formula $P_nO_{3n}^{-3}$ wherein $n$ is 3.

33. A method according to claim 26, any phosphate in said phosphate moiety other than pyrophosphate being selected from a ring phosphate of formula $P_nO_{3n}$ and one or more phosphates having the formula $P_nO_{3n+1}^{-(n+2)}$, where $n$ is less than 3, and combinations thereof.

34. A method according to claim 26, at least 50% of said phosphate moiety being said pyrophosphate the remaining phosphate moiety being phosphate selected from a ring phosphate of formula $P_nO_{3n}^{-n}$ and one or more phosphates of formula $P_nO_{3n+1}^{-(n+2)}$ of which not more than 15% by weight has an $n$ value greater than 2, and combinations thereof.

35. A method according to claim 26, wherein said stannous compound and phosphate are water soluble and the steps of admixing them, of adjusting the pH and of sterilizing said stannous-phosphate complex are carried out in a non-oxidizing atmosphere and under non-pyrogenic conditions, said step of admixing said stannous compound and phosphate being in aqueous solution, the water of which has been treated to remove oxygen and other oxidants which might cause oxidation of the stannous ion to a valence state greater than two.

36. A method according to claim 35, said pH adjustment step being carried out by addition of an alkaline pH adjusting agent pharmaceutically acceptable for intravenous injection to maintain said pH of 3 to 8, said sterile and non-pyrogenic stannous-phosphate complex being dried to a solid state and sealed in a sealed container under aseptic conditions and in a non-oxidizing atmosphere prior to admixing the same with said pertechnetate.

37. A method according to claim 36, said aqueous solution of sodium pertechnetate being a saline solution and being added to said stannous-phosphate complex under aseptic conditions, said stannous-phosphate complex being freeze dried.

* * * * *

UNITED STATES PATENT AND TRADEMARK OFFICE
CERTIFICATE OF CORRECTION

PATENT NO. : 4,016,249

DATED : April 5, 1977

INVENTOR(S) : Norman Adler and Leopoldo Camin

It is certified that error appears in the above-identified patent and that said Letters Patent are hereby corrected as shown below:

```
Column 2, line 2, after "uptake" insert --to uptake--
Column 4, line 6, "an" should be --and--
Column 5, line 9, "high" should be --highly--
Column 5, line 63, "99m" should be superscript
Column 6, line 33, after "dosage" insert --)--
```

Signed and Sealed this

Twenty-seventh Day of December 1977

[SEAL]

Attest:

RUTH C. MASON
*Attesting Officer*

LUTRELLE F. PARKER
*Acting Commissioner of Patents and Trademarks*